United States Patent [19]

Paterson

[11] Patent Number: 5,312,841
[45] Date of Patent: May 17, 1994

[54] WATER BASED BIOCIDE

[75] Inventor: Donald J. Paterson, Jacksonville, Fla.

[73] Assignee: Betz PaperChem, Inc., Jacksonville, Fla.

[21] Appl. No.: 898,974

[22] Filed: Jun. 15, 1992

[51] Int. Cl.$^5$ .................. A01N 33/12; A01N 41/10
[52] U.S. Cl. .................. 514/711; 514/642; 514/643
[58] Field of Search .................. 514/711, 642, 643

[56] References Cited

U.S. PATENT DOCUMENTS

| | | | |
|---|---|---|---|
| 3,426,134 | 2/1969 | Shema et al. | 424/302 |
| 3,896,231 | 7/1975 | Shema et al. | 424/304 |
| 3,996,155 | 12/1976 | Slovinsky et al. | 252/312 |
| 3,996,378 | 12/1976 | Payton | 424/302 |
| 4,671,815 | 6/1987 | Bellos et al. | 71/67 |

OTHER PUBLICATIONS

McCutcheon's Detergents and Emulsifiers pp. 18 and 22 (1971).

*Primary Examiner*—Allen J. Robinson
*Attorney, Agent, or Firm*—Alexander D. Ricci; Richard A. Paikoff

[57] ABSTRACT

The present invention relates to trihalo alkyl sulfone and mixtures of bis(trichloro methyl) sulfone (BTCMS), a non-ionic surfactant and a cationic quaternary ammonium halide surfactant formulated as a stable solution in water. The method of formulation comprises adding the BTCMS to an aqueous system containing a nonionic surfactant and a cationic quaternary ammonium halide surfactant. These formulations are useful as biocides and present advantages over organic solvent based formulations.

7 Claims, No Drawings

WATER BASED BIOCIDE

BACKGROUND OF THE INVENTION

This invention relates to the formulation of a stable, water based solution of trihaloalkyl sulfone. More particularly, the invention relates to the formulation of a stable, water based microemulsion of bis(trichloromethyl)sulfone (BTCMS), a nonionic surfactant and a cationic quaternary ammonium halide surfactant.

Manufacturing as well as production processes use huge quantities of raw as well as potable water that must be treated with biocides in order to assure product and production standards. Typically, cooling towers, paper and pulp mills, canning industries, animal hide processing plants, secondary oil recovery using water flooding, industrial water systems, to name a few, require the use and recycling of the water used in these processes. These systems become easily contaminated with microorganisms such as bacteria, algae, fungi, etc., due to exposure to contaminants encountered in the process of manufacturing and/or from the products being processed. These waters become a breeding media for microorganisms which must be controlled and/or eliminated. Biocides have been developed which control such contaminants which if left unchecked, will destroy equipment and/or reduce the quality of a manufactured product.

Many biocidal formulations involve the use of organic solvents. However, there are growing objections to the use of costly organic solvents in formulating biocides. Of extreme concern is the ecological impact of these organic solvents. The organic solvents typically used, for example dimethylformamide (DMF), are toxic by themselves. In addition, these solvents can accelerate in the ability of a biocide to penetrate human skin, so that in the case of spills or accidental contact, the danger to human life is increased. Other problems posed by utilizing organic solvents are low flash point, hence a fire hazard, and excessive repulsive odors.

Economic problems are a concern when the biocides are formulated using organic solvents. Organic solvents cost more and they can present processing problems so that the effect is to increase the cost of biocidal formulations containing organic solvents.

Recent changes in Environmental Protection Agency (EPA) regulations present additional difficulties by requiring the removal of solvent based products from the marketplace. Action has already been taken by the EPA against DMF. It is anticipated that action against other commonly used solvents for biocide formulations may be taken.

Accordingly, there is a need for alternatives to organic solvent based biocide formulations. It has now been discovered that trihaloalkyl sulfone, (specifically bis(trichloromethyl) sulfone) a nonionic surfactant and a cationic quaternary ammonium chloride can be formulated as stable microemulsions in water. The formulas of the present invention have shown biocidal efficacy essentially equivalent to the solvent based formulas.

These formulas avoid the disadvantages associated with the use of organic solvents. The inventive formulas result in a reduced risk to human life through accidental skin exposure. These novel solutions can be prepared so as to contain a variety of concentrations of active ingredients. The technique involved readily permits the introduction of other water-soluble biocides into the product solution.

Biocidal compositions which have relied on water as the carrier fluid for the water insoluble, solid, active materials have been either dispersions or "oil-in-water" macroemulsions of the biocidal active material (sulfone) dissolved in a hydrocarbon solvent. Both approaches may have included surfactants as stabilizers, as well as possible additional materials which modify the viscosity in order to prevent separation.

The dispersed particles, or droplets in the case of an emulsion, are typically in the range of about 2 to 2000 microns, as taught by Slovinsky in U.S. Pat. No. 3,996,155. Dispersions and emulsions with this particle or droplet size range are inherently unstable. During prolonged storage, these types of products are subject to coalescence, aggregation and separation. The present invention solves this inherent instability by producing a thermo-dynamically stable microemulsion, where the water insoluble actives have been solubilized through the use of a combination of surfactants.

Microemulsions generally have droplets significantly less than about 0.3 microns (u). A microemulsion with liquid oils as the dispersed phase has a typical droplet size range of about 100 to 700 angstroms (1 angstrom=0.0001u) and so is a transparent solution. This size range is two orders of magnitude smaller than typical dispersions and macroemulsions. Particle size measurements on the present invention generally show the size to be less than about 300 angstroms.

U.S. Pat. No. 4,671,815, Bellos et al., discloses solubilized biocidal active materials utilizing surface active alkylamine hydrochlorides. However, this reference states that water should not be present at levels above about 1.5%, with the preferred level less than about 0.75%. When water is present above this limit, the biocidal active precipitates. This is not a limitation with a microemulsion.

SUMMARY OF THE INVENTION

In the present invention, it has been discovered that blends comprising trihaloalkyl sulfone, a nonionic surfactant and a cationic quaternary ammonium halide surfactant can be prepared to form stable microemulsions in water. Optionally, a short chain alcohol may be added to the microemulsion. These mixtures have shown biocidal efficacy essentially equivalent to the corresponding organic solvent containing formula. The mixtures are also more effective than emulsions or dispersions with considerably larger particle size distributions using the same active concentrations.

DETAILED DESCRIPTION OF THE PREFERRED EMBODIMENTS

The trihaloalkyl sulfones utilized in the practice of the invention are bis(trichloromethyl) sulfone (BTCMS) and bis(tribromomethyl) sulfone (BTBMS), as disclosed by U.S. Pat. No. 3,426,134. The preferred sulfone is BTCMS.

Several classes of nonionic surfactants have been found to result in the formation of a microemulsion of sulfone in combination with several types of cationic quaternary amine surfactants. These classes of nonionic surfactants include alkyl phenol ethoxylates, alkanol ethoxylates, fatty acid ethoxylates, fatty acid polyethylene glycol esters, sorbitan fatty acid ester ethoxylates and poly(ethylene oxide): poly(propylene oxide) block copolymers. The nonionic surfactants, in conjunction with the cationic surfactant, vary in their ability to form a microemulsion. This is seen as necessitating more cationic surfactant in order to make the microemulsion. The most effective nonionic surfactants are alkanol ethoxylates and alkyl phenol ethoxylates with HLB ranges of from about 9 to 14. The preferred alkyl phenol ethoxylates are the nonyl and dodecyl phenols.

The concentration of nonionic surfactant may be between about 2% and 20% by weight, depending on the amount of sulfone included in the formula. It has been found that weight ratios of nonionic surfactant to sulfone from about 0.25:1 to 3:1 may be used. The preferred weight ratio is from about 0.5:1 to 1:1, which would correspond to concentrations between about 5% and 10%.

The cationic quaternary ammonium halide surfactants comprise alkyl aryl dimethyl ammonium chlorides and dialkyl dimethyl ammonium chlorides. Examples of alkyl aryl dimethyl ammonium chlorides are alkyl benzyl dimethyl ammonium chlorides, where the alkyl group contains about 8 to 18 carbon atoms. Examples of dialkyl dimethyl ammonium chlorides are dioctyl and didecyl dimethyl ammonium chlorides. The preferred cationic quaternary amine surfactants are biocidally active alkyl dimethyl benzyl ammonium chlorides, where the alkyl chain length is between about 8 to 18 carbon atoms.

The concentration of cationic surfactant needed to form a microemulsion depends on the type of nonionic surfactant used. The concentration of cationic surfactant may be between about 5% and 40%. Using the preferred alkyl phenol ethoxylates, the concentration of cationic surfactant may be between about 5% and 30%. The preferred range is between about 8% and 30%.

Representative examples of nonionic surfactants are listed in Table 1. The amount of cationic surfactant (alkyl benzyl dimethyl ammonium chloride) needed to form a microemulsion is also shown. It can be seen that the amount of cationic surfactant needed to form the microemulsion depends on factors such as HLB and the chemical nature of the nonionic surfactant.

The method used to evaluate the nonionic surfactants entailed emulsifying the sulfone with the nonionic surfactant at about 130° F. followed by cooling to ambient temperature. Cationic surfactant was added incrementally to the intermediate macroemulsions until the microemulsions were formed.

TABLE 1

| Nonionic Surfactant | HLB | Required % Cationic Surfactant |
|---|---|---|
| Ethoxylated Primary Alcohol | 7.0 | 23.3 |
| | 8.0 | 20.6 |
| | 9.0 | 18.1 |
| | 10.0 | 18.6 |
| | 12.2 | 14.4 |
| | 12.5 | 15.8 |
| | 13.3 | 15.2 |
| Ethoxylated Secondary Alcohol | 8.0 | 30.2 |
| | 8.3 | 29.9 |
| | 10.5 | 20.2 |
| | 12.8 | 18.7 |
| | 14.5 | 26.1 |
| | 16.1 | 27.7 |
| | 17.4 | 31.0 |
| Ethoxylated Dialkylphenol | 10.6 | 18.6 |
| | 15.0 | 30.8 |
| Ethoxylated Dodecylphenol | 10.0 | 17.6 |
| | 12.1 | 15.3 |
| | 12.6 | 21.3 |
| | 13.4 | 31.7 |
| EO/PO Block Copolymer | 8.0 | 71.3 |

TABLE 1-continued

| Nonionic Surfactant | HLB | Required % Cationic Surfactant |
|---|---|---|
| | 9.0 | 23.5 |
| | 13.0 | 21.2 |
| | 27.0 | 30.5 |
| Ethoxylated Nonylphenol | 8.8 | 18.6 |
| | 10.8 | 19.4 |
| | 12.9 | 14.0 |
| | 13.0 | 18.1 |
| | 13.6 | 14.4 |
| | 14.2 | 18.8 |
| Ethoxylated Nonylphenol | 15.0 | 31.5 |
| | 16.0 | 32.2 |
| | 17.8 | 35.7 |
| | 19.0 | 40.3 |
| Ethoxylated Oxtylphenol | 12.0 | 18.9 |
| | 12.4 | 18.6 |
| | 13.5 | 28.9 |
| | 14.6 | 33.8 |
| | 17.3 | 34.5 |
| | 18.0 | 34.4 |
| Polyethylene Glycol Esters | 5.0 | 44.3 |
| | 7.8 | 53.9 |
| | 8.1 | 24.7 |
| | 9.8 | 25.6 |
| | 10.5 | 22.6 |
| | 11.0 | 28.6 |
| | 13.5 | 26.7 |
| | 15.6 | 29.2 |
| | 16.8 | 30.1 |
| | 18.4 | 24.1 |

The optional short chain aliphatic alcohols comprise alcohols with between about 1 and 8 carbon atoms. The alcohols may be primary, secondary or tertiary, depending on chain length. Examples include methanol, ethanol, 1-propanol, 2-propanol, 1-butanol, 2-butanol, 1-pentanol, 2-pentanol and 1-hexanol. The preferred alcohols are propanols and butanols. A stable microemulsion may be formed without the short chain alcohol. However, the inclusion of the short chain alcohol results in a microemulsion which is stable to multiple freeze/thaw cycles.

The preparation of the microemulsion is accomplished by blending the appropriate amount of water, nonionic surfactant and cationic surfactant until uniform and heating to about 130° F. The appropriate amount of sulfone is then added. The sulfone may be added either as a crystalline solid, or melted and added as a liquid. The blend is then cooled to below about 90° F. A short chain aliphatic alcohol may then be optionally added.

It has been found that up to about 15% sulfone may be used in order to create the microemulsion. A minimum amount of cationic surfactant is used to form the microemulsion. A minimum ratio of sulfone to cationic surfactant of about 0.25:1 may achieve the microemulsion. The preferred ratio is about 0.75:1 to 3:1.

The biocidal activity of the microemulsion formulation has been compared to both a commercially available solvent-based product and a water-based dispersion. Compared to the water-based dispersion, where the particle size is typically in the range of 2 to 2000 microns, the microemulsion formulations show superior efficacy, typically by about 20% to 25%.

TABLE 2

| | Biocidal Efficacy Comparison | | |
|---|---|---|---|
| Sample | % Wt. Sulfone | % Wt. Quaternary Amine | Inhibition (ppm) ($I_{50}$ Value)* |
| Solvent based | 20.0 | 15.0 | 26 |

TABLE 2-continued

Biocidal Efficacy Comparison

| Sample | % Wt. Sulfone | % Wt. Quaternary Amine | Inhibition (ppm) ($I_{50}$ Value)* |
|---|---|---|---|
| | 10.0 | 10.0 | 50 |
| Water Based Dispersion | 10.0 | 10.0 | 74 |
| Microemulsion A | 10.0 | 8.0 | 51 |
| Microemulsion B | 10.0 | 10.0 | 52 |
| Microemulsion C | 10.0 | 12.0 | 48 |
| Sulfone (solvent based) | 10.0 | 0.0 | 255 |
| Quaternary Amine | 0.0 | 10.0 | 94 |

*Concentration of biocidal agent to achieve 50% reduction in bacterial growth compared to an untreated control.

An additional study investigated the effects of sulfone content on the efficiency of the microemulsion. The results of this study show that a significant increase in efficacy occurs with the addition of up to about 5% sulfone in the microemulsion. This effect is seen at various quaternary amine levels.

TABLE 3

Effect of Sulfone Content on Efficacy

| % Wt. Sulfone | % Wt. Quaternary Amine | Inhibition (ppm) ($I_{50}$ Value) |
|---|---|---|
| 0.00 | 8.0 | 162 |
| 1.00 | 8.0 | 64 |
| 3.25 | 8.0 | 72 |
| 5.50 | 8.0 | 69 |
| 7.75 | 8.0 | 68 |
| 10.00 | 8.0 | 51 |
| 0.00 | 10.0 | 121 |
| 1.00 | 10.0 | 77 |
| 3.25 | 10.0 | 55 |
| 5.50 | 10.0 | 58 |
| 7.75 | 10.0 | 60 |
| 10.00 | 10.0 | 62 |
| 0.00 | 12.0 | 103 |
| 1.00 | 12.0 | 58 |
| 3.25 | 12.0 | 52 |
| 5.50 | 12.0 | 64 |
| 7.75 | 12.0 | 50 |
| 10.00 | 12.0 | 48 |

While we have shown and described herein certain embodiments of the present invention, it is intended that there be covered as well any change or modification therein which may be made without departing from the spirit and scope of the invention.

I claim:

1. A biocidal formulation comprising a water based, stable solution of:
   a) about 1–20% by weight of bis(trichloro methyl) sulfone or bis(tribromo methyl) sulfone;
   b) about 2–20% by weight of a nonionic surfactant; and
   c) about 5–40% by weight of a cationic quaternary ammonium halide surfactant.

2. The biocidal formulation as recited in claim 1 further comprising a short chain aliphatic alcohol.

3. The biocidal formulation as recited in claim 1 wherein said solution is in the form of a microemulsion.

4. The biocidal formulation as recited in claim 1 wherein the nonionic surfactant is selected from the group consisting of alkyl phenol ethoxylates, alkanol ethoxylates, fatty acid ethoxylates, fatty acid polyethylene glycol esters, sorbitan fatty acid ester ethoxylates and ethylene oxide/propylene oxide block copolymers.

5. The biocidal formulation as recited in claim 4 wherein the hydrophile/lipophile balance of the nonionic surfactant is from about 9 to 14.

6. The biocidal formulation as recited in claim 1 wherein the weight ratio of nonionic surfactant to sulfone is from about 0.25:1 to 3:1.

7. The biocidal formulation as recited in claim 1 wherein the cationic quaternary ammonium halide surfactant is selected from the group consisting of alkyl aryl dimethyl ammonium chlorides and dialkyl dimethyl ammonium chlorides.

* * * * *